United States Patent [19]

Langdon

[11] Patent Number: 5,323,638
[45] Date of Patent: Jun. 28, 1994

[54] SENSOR APPARATUS

[75] Inventor: Roger M. Langdon, Colchester, United Kingdom

[73] Assignee: GEC-Marconi Limited, United Kingdom

[21] Appl. No.: 866,050

[22] Filed: Apr. 10, 1992

[51] Int. Cl.$^5$ ............................ G01N 9/34; G01N 11/16
[52] U.S. Cl. ...................................... 73/32 A; 73/54.27
[58] Field of Search .................. 73/32 A, 54.24, 54.27

[56] References Cited

U.S. PATENT DOCUMENTS 4,922,745  5/1990  Rudin et al. ...................... 73/32 A

FOREIGN PATENT DOCUMENTS

0102490A1  7/1983  European Pat. Off.
3611632   10/1986  Fed. Rep. of Germany ..... 73/32 A
27219      8/1971  Japan ................................ 73/32 A
1143040    7/1967  United Kingdom .

OTHER PUBLICATIONS

R. M. Langdon, "Vibratory Process Control Transducers", Marconi Review, vol. 43, No. 218 (Third Quarter 1980), pp. 156–175.

Primary Examiner—Hezron E. Williams
Assistant Examiner—Joseph W. Roskos
Attorney, Agent, or Firm—Lowe, Price, LeBlanc & Becker

[57] ABSTRACT

A sensor, for use in determining physical properties of fluid, comprises a flexible diaphragm having a plane. Two tines depend from the diaphragm substantially at right angles to the plane. First and second substantially planar transducers are each bonded to the diaphragm so that the plane of the transducers are parallel to that of the diaphragm. A first one of the transducers is operative, in use, to flex between in its plane and to couple an alternating driving force into the plane of the diaphragm such that the tines vibrate in an oscillatory motion. Second of the transducers is operative to detect vibrations of the diaphragm.

16 Claims, 3 Drawing Sheets

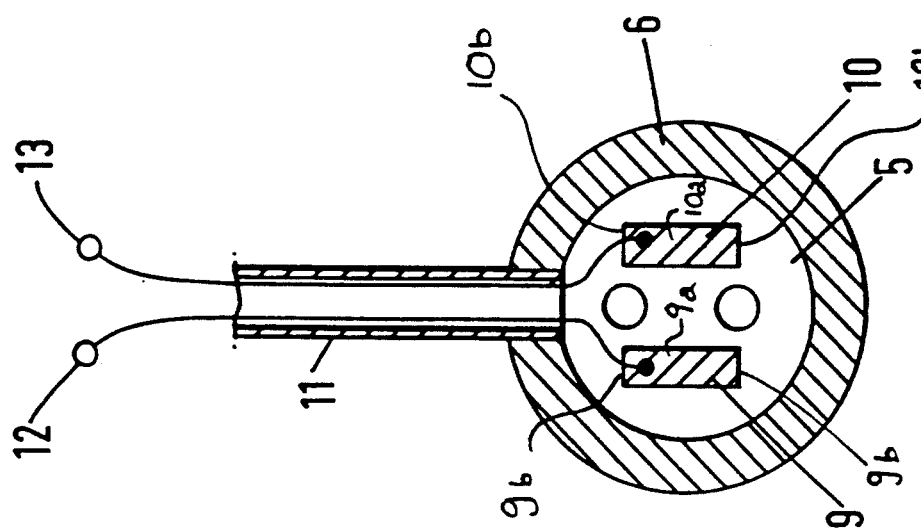
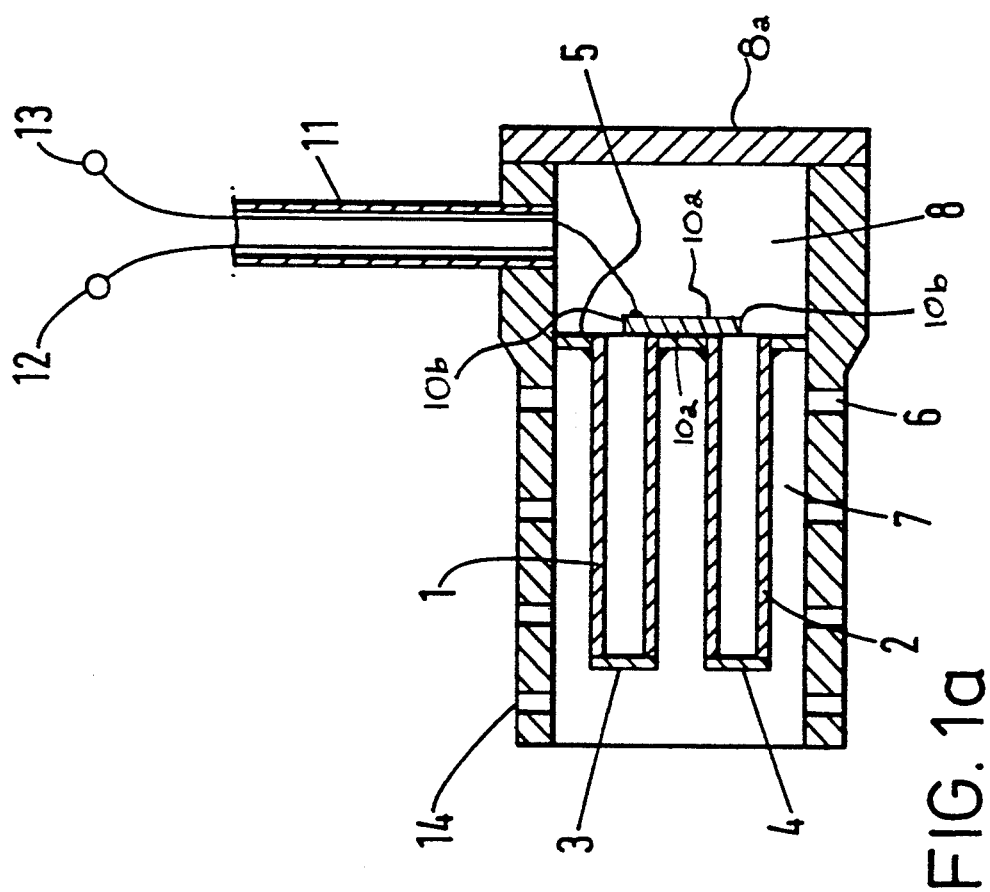
FIG. 1a
FIG. 1b

SENSOR APPARATUS

FIELD OF THE INVENTION

This invention relates to sensor apparatus and more particularly, but not exclusively, to sensors which are suitable for measuring the viscosity and/or density of liquids which tend to produce contamination of sensor surfaces.

DESCRIPTION OF THE PRIOR ART

A number of methods are known for measuring the viscosity of a liquid using a vibrating sensor. One such sensor consists of a rectangular metal strip excited into longitudinal resonant vibrations by a magnetostrictive driver. The presence of a liquid in contact with the surface of the vibrating strip causes the decay time of the vibration to change in a way which is dependent on the liquid viscosity and density. Measuring the decay time of the vibration when the source of excitation is removed therefore provides a means for measuring the liquid viscosity if the liquid density is known.

A disadvantage of such sensors is that they operate at ultrasonic frequencies (20 kHz or more) which render them sensitive to surface contamination. This arises because the depth of penetration of the shear wave into the body of the liquid caused by the oscillatory motion of the sensor is inversely dependent on the oscillation frequency. At ultrasonic frequencies, the penetration depth of the shear wave into the liquid only extends a few micrometers from the sensor surface. Layers of surface contamination on the sensor arising from deposited solids therefore cause a major alteration in sensor characteristics. In the case of sensors measuring the viscosity of frying oils, this is of particular importance because of surface contamination arising from chemical changes within the oil during its life.

U.S. Pat. No. 4,922,745 in the name of Rudkin et al discloses a number of sensors each having a pair of elongate vibratory tines joined by a yoke and including a transducer which is operative, in use, to generate an alternating driving force to set the tines into an oscillatory motion. In each case the transducers are mounted under compression and are arranged to act in the same sense as the direction of elongation of the tines.

The degree of compression would be critical to the operation of the device and, in the applicants opinion, it would be difficult to repeatedly manufacture such sensors having similar operational characteristics.

The Marconi Review Vol. 43 No. 218 (Third Quarter 1980) discloses, in an article entitled "Vibratory Process Control Transducers" by R. M. Langdon on Pages 156–175, a sensor comprising a pair of tines connected by a yoke and where piezoelectric transducers are bonded to an inside wall of the tines.

During manufacture, the transducers must be held tightly against the wall of the tine until they have bonded and their location thus limits the length of the transducer that can be used. A relatively longer transducer will give a larger deflection per unit applied voltage. Again, as with the patent to Rudkin, the transducers each act in the same sense as the direction of elongation of the tine.

The present invention arose from an attempt to provide a sensor which is particularly suitable for sensing the viscosity and/or density of liquids such as frying oils and which can be made available repeatedly at low cost and without the need for extensive calibration.

SUMMARY OF THE INVENTION

According to the invention there is provided a sensor, for use in determining physical properties of a fluid, comprising a flexible diaphragm having a plane, two tines depending from said diaphragm substantially at right angles to the plane of said diaphragm, first and second substantially planar transducers each bonded to said diaphragm such that the plane of each transducer is parallel to the plane of said diaphragm, a first of said transducers being operative, in use, to flex in its plane and to couple an alternating driving force into the plane of the diaphragm such that the tines vibrate in an oscillatory motion, the second of said transducers being operative to detect vibrations of the diaphragm.

The diaphragms can be made repeatedly to a thickness within fine tolerances and the fact that the transducers are bonded to the diaphragm ensures that it is possible to predict, with a small margin of error, the resultant amplitude of deflection of the diaphragm. The construction also allows a relatively long face of a transducer to be in contact with the diaphragm which can ensure a relatively large deflection per unit applied voltage. In contrast to the earlier patent to Rudkin and the aforementioned article by Langdon, each of the transducers can apply a driving force directly into the plane of the diaphragm, as opposed to the direction of elongation of a respective tine.

By employing the invention, it is possible to use a much lower frequency of around only a few hundred Hertz to measure the viscosity, thus making sensor apparatus in accordance with the invention particularly suitable for use with fluids such as frying oils in which chemical changes occur. The sensor apparatus may be made sufficiently compact for hand-held use and also enables the fluid density and viscosity to be independently calculated from measurements of the vibration characteristics of the vibratory structure.

In operation, the tines will vibrate such that their free ends will move towards and away from one another. The tines are advantageously hollow tubes, which are lightweight structure exhibiting suitable vibratory properties. Where piezoelectric transducers are used to apply the driving force and to detect the resultant vibration of the members, they are advantageously fixed to the surface of the diaphragm other than that from which the members are extensive.

The elongate transducers preferably extend parallel to one another on either side of a line joining the centres of the two depending tines.

Preferably the sensor further comprises means for applying an alternating driving force of successive different frequencies to the first transducer, and means, connected to the second transducer, for comparing the vibrational movement of the diaphragm with the driving force to determine the viscosity and/or density of a fluid in which the tines are immersed.

It can be shown that, when sensor apparatus in accordance with the invention is immersed in a liquid of density $\rho$ and dynamic viscosity $\eta$, and when a drive transducer, for example, for causing the vibratory structure to vibrate is driven by a sinusoidal voltage of amplitude $V_i$ represented by th real part of the expression $$V_i = V_i' \exp(j\omega t) \quad (1)$$

where $V_i$ is the peak voltage, $\omega$ is the angular frequency and t is the time, the ratio of output voltage $V_o$ from a detecting transducer to input voltage $V_i$ is given by $$V_o/V_i = C/(\omega^2 - \omega_1^2 + 2j\alpha\omega) \quad (2)$$

where C is a constant, $\omega$ is the damping constant and $\omega_1$ (the resonance frequency in the liquid) is given by the expression $$\omega_1 \omega_0 / [1 + K\rho + 2K(2\eta\rho/\omega)^{\frac{1}{2}}/R]^{\frac{1}{2}} \quad (3)$$

where K is a constant and R is the outer radius of the members. The damping constant, is given by the expression $$\alpha = \frac{\alpha_o + K(2\omega\eta\rho)^{\frac{1}{2}}/R}{1 + K\rho + 2K(2\eta\rho/\omega)^{\frac{1}{2}}/R} \quad (4)$$

where $\alpha_o$ is a constant and $\omega_o$ is the resonance frequency in vacuum. Sweeping the drive frequency $\omega$ on either side of the resonance frequency $\omega_1$ and measuring the real and imaginary parts of the output/input ratio $V_o/V_i$ enables the quantities $\omega_1$ and $\alpha$ to be calculated. The liquid viscosity and density can then be calculated using equations (3) and (4).

It is preferred that the alternating driving force is arranged to vary such that the structure vibrates at at least one frequency greater than and less than its resonance frequency in the fluid, although the frequencies could be on the same side of the resonant frequency.

In one embodiment of the invention, it is preferred that the means for comparing measures the ratio of the magnitude of the driving force to the magnitude of the vibrational movement.

In the case of low viscosity liquids, the damping factor $\alpha$ is very much smaller than the angular resonance frequency $\omega_1$. Under those conditions, the damping factor can be readily measured by measuring the frequencies on either side of the resonance frequency for which there is a 90°±45° phase shift between output and input voltages. It can be shown that if those angular frequencies are $\omega_a$ and $\omega_b$ then $$\alpha \approx (\omega_a - \omega_b)/2 \quad (5)$$

If the density of the liquid is approximately known, which is true in the majority of cases, then equation (4) can be approximated to $$\alpha \approx K_1 + K_2(\eta)^{\frac{1}{2}} \quad (6)$$

where $K_1$ and $K_2$ are constants, from which the liquid viscosity $\eta$ may be calculated. The size of the constants in the above expressions are functions of the geometry of the sensor and need to be established by prior calibration.

In one preferred embodiment of the invention, therefore, means are included for determining the difference between the frequencies of vibration of the structure for which the phase difference between the driving force and the vibrational movement is substantially 135° and 45° respectively.

In a preferred embodiment of the invention, the means for applying a alternating driving force includes a piezoelectric transducer to which an alternating voltage is applied, the transducer advantageously being attached to a surface of the vibratory structure. Also it is preferable that the means for detecting the vibratory movement of the members includes a piezoelectric transducer.

BRIEF DESCRIPTION OF THE DRAWINGS

One way in which the invention may be performed is now described by way of example with reference to the accompanying drawings in which:

FIGS. 1A and 1B are longitudinal and transverse sections respectively of a sensor in accordance with the invention;

DESCRIPTION OF THE PREFERRED EMBODIMENT

Figure 2:
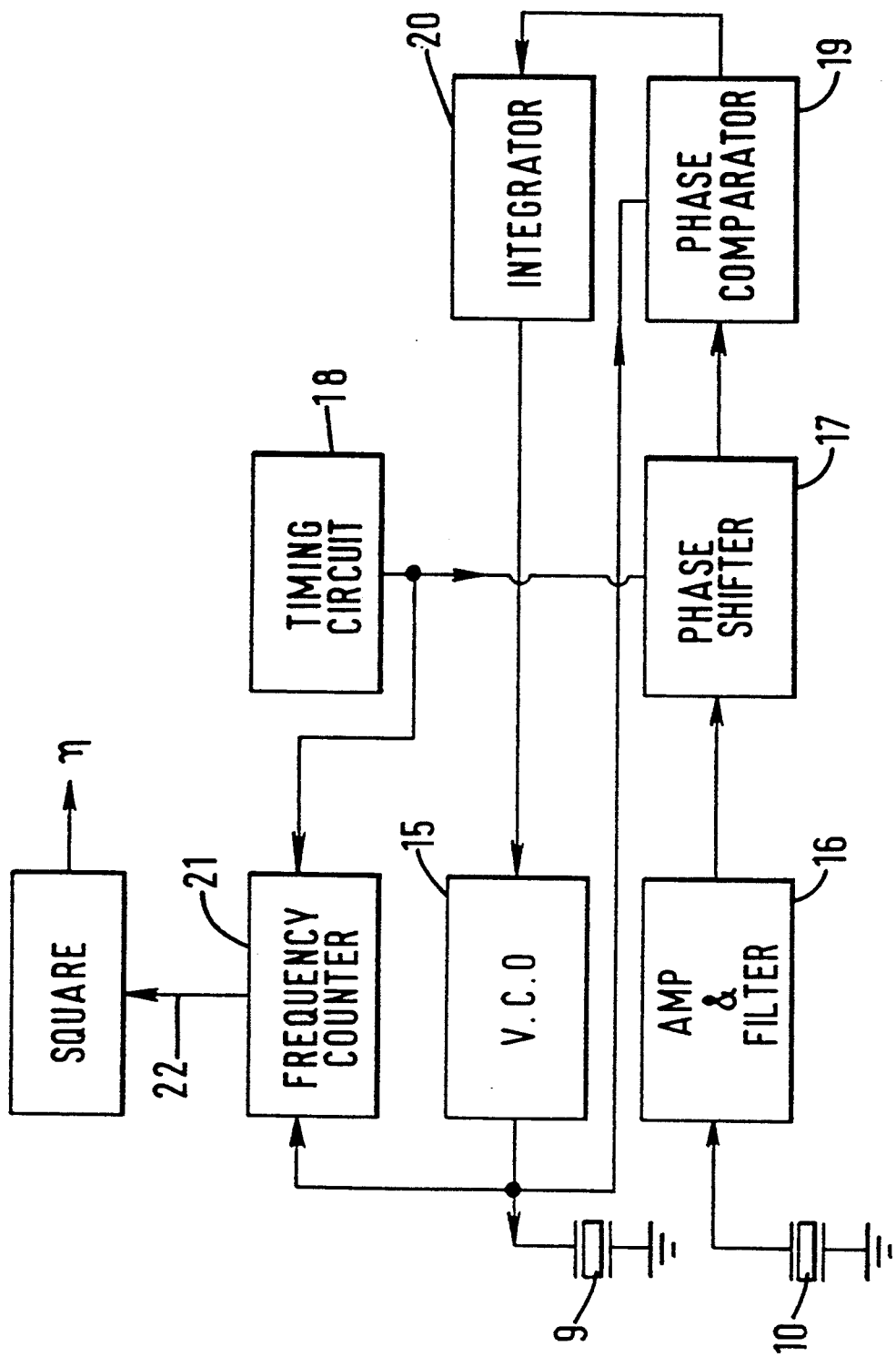
FIG. 2 is a block schematic diagram of circuitry associated with the sensor.

With reference to FIGS. 1A and 1B, a sensor includes two tines comprising stainless steel tubes 1 and 2 of the same length and diameter which are sealed, each at one end, by stainless steel sealing caps 3 and 4. The other ends of the tubes 1 and 2 are welded into two holes in a stainless steel circular diaphragm 5, being symmetrically disposed about the centre of the diaphragm. The periphery of the diaphragm is fixed to the inside surface of a cylindrical housing 6, forming two compartments 7 and 8 within the housing 6 separated by the diaphragm 5. Two rectangular substantially planar plates 9 and 10 of a piezoelectric ceramic material, such as lead zicronate-titanate, each include a pair of longer faces 9a, 10a respectively intermediate a pair of ends 9b, 10b. One of the longer faces 9a, 10a is bonded, e.g. by soldering or a suitable adhesive, to a surface of the diaphragm other than that from which the tubes 1 and 2 project. The piezoelectric plates 9 and 10 are attached near the centre of the diaphragm 5 with their long sides parallel to a line joining the centres of the tubes 1 and 2, the plates 9 and 10 being symmetrically positioned about the centre of the diaphragm 5.

The compartment 8 of the housing 6 which contains the piezoelectric plates 9 and 10 is sealed by a lid 8a and has a tube 11 providing access to the enclosed cavity. The uppermost face, as shown of each plate 9, 10 does not touch the walls of the compartment 8, and the plates 9, 10 are thereby uncompressed. Electrical leads 12 and 13 are conducted into the compartment 8 through the tube 11 and are connected to electrodes on the surfaces of the piezoelectric plates 9 and 10. The tube 11 is of sufficient length such that the housing 6 may be fully immersed in a liquid, the viscosity of which is to be monitored, whilst its open end and emerging leads 12 and 13 are above the surface of the liquid. A plurality of holes 14 through the wall of the housing 6 around the outer compartment 7 allows free flow of liquid over the tubes 1 and 2 when the sensor is immersed. Thus, the outer surfaces of the tubes 1 and 2 are covered by the liquid whilst the inner surfaces of the tubes and the interior of the enclosed compartment 8, including the piezoelectric plates 9 and 10, remain dry.

During operation, a voltage is applied to a surface electrode on one of the piezoelectric plates 9, producing a stress in the plane of the plate 9 by the transverse piezoelectric effect. This causes the plate 9 and the diaphragm 5 to bend slightly, such that the free ends of the tubes 1 and 2 move closer together. When the voltage applied to the piezoelectric plate 9 is reversed, the tips of the tubes 1 and 2 move further apart. Thus, application of an alternating voltage to the piezoelectric transducer 9 causes oscillatory vibration of the tubes 1 and 2 in the manner of a tuning fork. If the frequency of the alternating drive voltage is equal, or near, to the flexural resonance frequency of the tube/diaphragm vibrating structure, then a large amplitude of vibration builds up. The voltage produced on the surface electrode of the other piezoelectric plate 10 is proportional to the vibrational displacement of the tubes 1 and 2 and so provides a measure of the phase of the tube displacement relative to the phase of the alternating drive voltage.

With reference to FIG. 2, a voltage controlled oscillator 15 drives the piezoelectric plate 9 at a range of frequencies on either side of its resonant frequency when the sensor is immersed in liquid. The open circuit output from the second piezoelectric plate 10 is amplified and filtered at 16 to remove unwanted frequencies arising from vibration of machinery and other sources. The filtered signal is applied to a switched phase shifter 17 which switches the phase by 90°±45°. The phase shifter 17 is operated by a timing circuit 18 which generates equal amounts of the two phases in sequence, with a period of approximately one second. The output from the phase shifter 17 is applied to a phase comparator 19 which also receives a signal from the voltage controlled oscillator 15. The comparator 19 compares the phase shifted signal with the output of the oscillator 15 to produce an output voltage which is proportional to the phase difference. This is integrated by an integrator 20 to remove high frequency fluctuations and the integrated output applied to the frequency control input of the voltage controlled oscillator 15.

The circuit is adjusted to give the two required angular frequencies corresponding 90°±45° phase difference between the drive and output voltages. When the phase shifter 17 is set to 90°±45°, a frequency counter 21 counts the number of cycles in the output of the oscillator 15 during the measurement interval. During the second timing interval, when the phase shifter is set to 90°−45°, the frequency counter 21 is set into a reverse mode such that it counts down for the duration of the second measurement interval. The residual count at the end of the second interval is thus proportional to the angular frequency difference. This process may be repeated over a number of consecutive timing cycles to yield a value for the difference frequency with improved accuracy. Once the quantity proportional to the angular frequency difference has been measured, the liquid viscosity can then be established using equations (5) and (6).

In many cases, the first term in equation (6) may be made much smaller than the second so that a numerical quantity proportional to viscosity may be obtained simply by squaring the residual count from counter 21 at 22.

Figure 3:
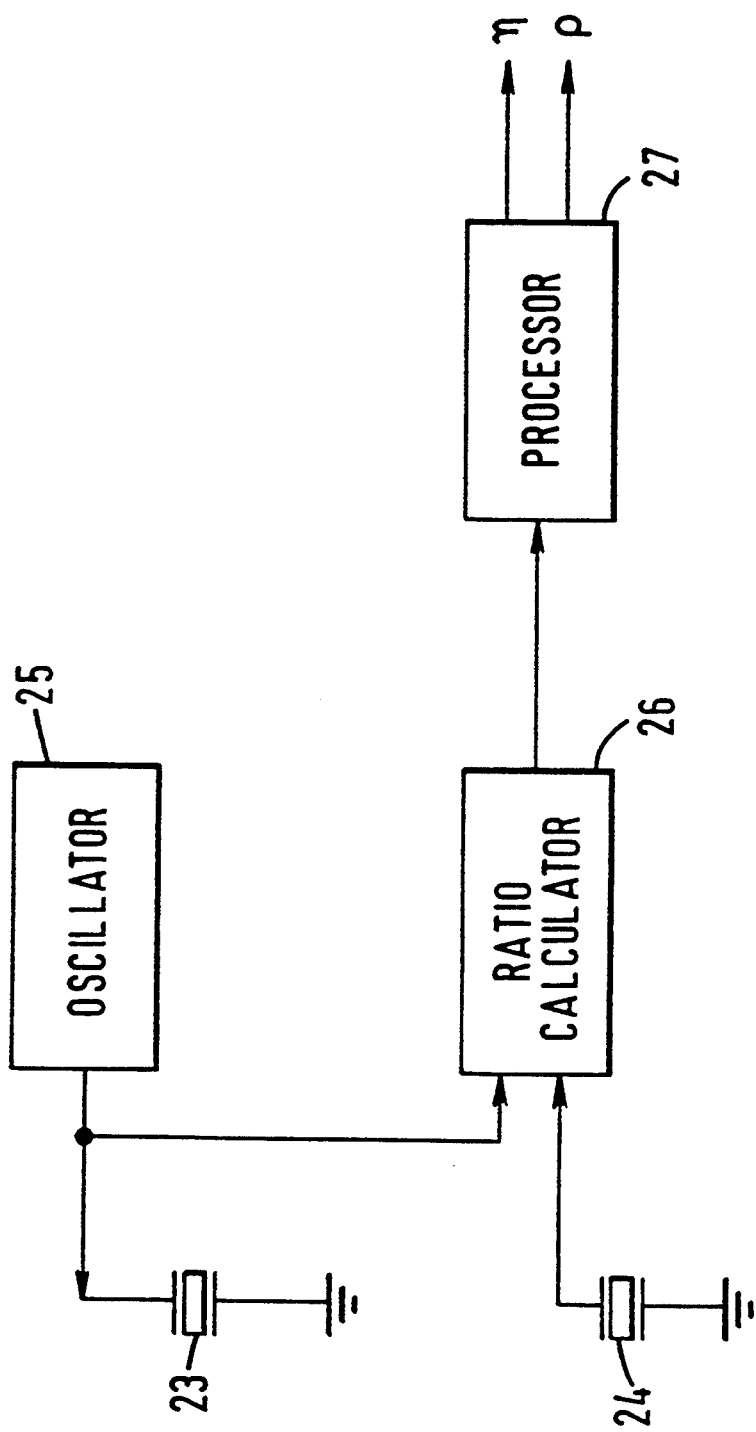
FIG. 3 is a block schematic diagram of another sensor in accordance with the invention.

The sensor described with reference to FIGS. 1A, 1B and 2 is suitable for use with low viscosity liquids. If it is wished to measure the properties of higher viscosity liquids, the arrangement illustrated in FIG. 3 may be used. The vibrating structure is the same as that shown in FIGS. 1A and 1B; Piezoelectric transducers 23 and 24 respectively drive the structure into vibration and detect its vibration. The drive voltage is applied to the transducer 23 from an oscillator 25 having a swept frequency output. The ratio of the output voltage from the detecting transducer 24 to the drive voltage is determined at 26. The output of 26 is applied to a processor circuit 27 which calculates the resonance frequency and damping constant and determines the viscosity and density of the liquid using equations (3) and (4).

I claim:

1. A sensor, for use in determining physical properties of a fluid, comprising a flexible diaphragm having a plane, two tines depending from said diaphragm substantially at right angles to the plane of said diaphragm, first and second substantially planar transducers each bonded to said diaphragm such that the plane of each transducer is parallel to the plane of said diaphragm, a first of said transducers being operative, in use, to flex in its plane and to couple an alternating driving force into the plane of the diaphragm such that the tines vibrate in an oscillatory motion, the second of said transducers being operative to detect vibrations of the diaphragm.

2. A sensor, according to claim 1, wherein the diaphragm includes two opposed faces, the tines depend from one of said faces and the transducers are bonded to the other of said faces.

3. A sensor, according to claim 1, in which the planar transducers are elongate and each extend parallel to one another on either side of a line joining the centres of the two depending tines.

4. A sensor, according to claim 3, wherein the two transducers are of substantially the same length as the spacing between the centres of the two tines.

5. A sensor, according to claim wherein the transducers are located within an enclosed compartment having walls and where each transducer is uncompressed by the walls of the compartment.

6. A sensor, according to claim 1, wherein the diaphragm is circular and the transducers are disposed symmetrically about the centre of the diaphragm.

7. A sensor, according to claim 1, wherein the tines are hollow tubes.

8. A sensor, as claimed in claim 1, wherein the transducers are piezo-electric transducers.

9. A sensor, as claimed in claim 1, further comprising a wall surrounding the tines, the wall having apertures therethrough through which the fluid to be measured can pass.

10. A sensor, according to claim 1, further comprising means for applying an alternating driving force of successive different frequencies to the first transducer, and means, connected to the second transducer, for comparing the vibrational movement of the diaphragm with the driving force to determine the viscosity and/or density of a fluid in which the tines are immersed.

11. A sensor, as claimed in claim 10, wherein the frequency of the alternating driving force is arranged to vary such that the tines vibrate at at least one frequency greater than and one frequency less than the resonant frequency of the tines in the fluid.

12. A sensor, as claimed in claim 10, wherein the means for comparing measures the ratio of the magnitude of the driving force to the magnitude of the vibrational movement.

13. A sensor, as claimed in claim 10, wherein the means for comparing compares the phase of the vibrational movement with the phase of the driving force.

14. A sensor, as claimed in claim 13, and including means for determining the difference between the frequencies of vibration of the elongate members for which the phase difference between the driving force and the vibrational movement is substantially 135° and 45° respectively.

15. A sensor, as claimed in claim 14, wherein the frequency of the driving force is switched at equal time intervals between the two values which produce the phase differences of 135° and 45° and including a frequency counter for counting the number of cycles of the frequency during each time interval, whereby the difference in frequency is determined.

16. A sensor, as claimed in claim 10, and including a phase locked loop to control the frequency of the driving force.

* * * * *